United States Patent
Hollingsworth

(10) Patent No.: US 6,239,311 B1
(45) Date of Patent: May 29, 2001

(54) PROCESS FOR THE PREPARATION OF 3,4-DIHYDROXYBUTANOIC ACID AND SALTS AND LACTONES DERIVED THEREFROM

(75) Inventor: Rawle I. Hollingsworth, Haslett, MI (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

(21) Appl. No.: 09/556,532

(22) Filed: Apr. 24, 2000

(51) Int. Cl.[7] .................................................. C07C 51/00
(52) U.S. Cl. ............................................................ 562/515
(58) Field of Search ............................................... 562/515

(56) References Cited

U.S. PATENT DOCUMENTS 5,292,939 * 3/1994 Hollingsworth .
5,319,110 * 6/1994 Hollingsworth .
5,374,773 * 12/1994 Hollingsworth .

FOREIGN PATENT DOCUMENTS

513430 * 11/1992 (EP) .

OTHER PUBLICATIONS

Corbett, W.M., et al., J. Chem. Soc., 1431–1435 (1955).
Green, J.W., J. Amer. Chem. Soc. 78:1894–1897 (1956).
Moody, G. J., Advances in Carbohydr. Chem. 19: 149–180 (1964).
Glattfield, J.W.E., et al., J. Amer. Chem. Soc. 40:973 (1918).
Hollingsworth, R., J. Org. Chem. 64:7633–7634 (1999).
Huang, G. and R. I.Hollingsworth, Tetrahedron 54:1355–1360 (1998).
Nakamura, N., et al., Tetrahedron Letters, 30: 2245–2246 (1989).
Zhou, B., et al., J. Amer. Chem. Soc. 105:5925–5926 (1983).
Uchikawa, O., et al., Bull. Chem. Soc. Jpn. 61–2025–2029 (1988).
Hayashi, H., et al., J. Amer. Chem. Soc. 95: 8749–8757 (1973).
Danklmaier, J., et al., Liebigs. Ann. Chem. 1149–1153 (1988).
Mori, Y., et al., Tetrahedron Letts. 29 5419–5422 (1988).
Shieh, H.M., et al., Tetrahedron Letts 23:4643–4646 (1982).
Mori, K., et al., Tetrahedron Letts 29:5423–5426 (1988).
Saito, S., et al., Chem. Letts 1389–1392 (1984).
Wu, G., et al., J. Org. Chem. 64 3714–3718 (1999).
Song, J., et al., J. Amer. Chem. Soc 121 1851–1861 (1999).
Wang, G., et al., J. Org. Chem. 64 1036–1038 (1999).
Huang, G., et al., Tetrahedron Asymmetry 9 4113–4115 (1999).
Wang, G., et al., Tetrahedron Assym. 10 1895–1901 (1999).

* cited by examiner

Primary Examiner—Ralph Gitomer
Assistant Examiner—D. Khare
(74) Attorney, Agent, or Firm—Ian C. McLeod

(57) ABSTRACT

An improved process for the preparation of 3,4-dihydroxybutanoic acid (1) and salts thereof from a D- or L-hexose source is described. The process uses an alkali metal or alkaline earth metal hydroxide and peroxide oxidizing agent to convert the D- or L-hexose source to (1) by maintaining a low concentration of base and oxidizing agent in the reaction mixture at any one time and by maintaining a temperature between about 25° C. and 80° C. Upon acidification of the reaction mixture the 3-hydroxylactone is produced. The compound (1) is useful as a chemical intermediate to naturally occurring fatty acids and is used to prepare 3,4-dihydroxybutanoic acid-gamma-lactone (2) and furanone (3), particularly stereoisomers of these compounds.

55 Claims, 2 Drawing Sheets

PROCESS FOR THE PREPARATION OF 3,4-DIHYDROXYBUTANOIC ACID AND SALTS AND LACTONES DERIVED THEREFROM

BACKGROUND OF THE INVENTION (1) Field of the Invention

The present invention relates to an improved process for preparation of 3,4-dihydroxybutanoic acid, glycolic acid and salts thereof from a D- or L-hexose source, particularly a D- or L-glucose source, containing glucose as a substituent. Further, the present invention relates to a process for preparing lactones derived from (S)-3,4-dihydroxybutanoic acid and salts thereof.

(2) Prior Art

During the course of the development by syntheses of naturally-occurring (R)-3-hydroxy long chain fatty acids, various synthetic routes to (S)-4-bromo-3-hydroxybutanoic acid methyl or ethyl esters were examined. The general approach was to carve out this chiral fragment from a suitably modified carbohydrate structure. Initial attempts involved selective protection and structural modification of methyl alpha-D-glucopyranoside followed by cleavage to yield a 4-carbon fragment containing the required functionalities. Although this approach proved to be quite viable, it proved not to be as direct as was believed.

A reaction in which some of the desired product is generated in fewer steps from inexpensive starting materials was considered. The treatment of cellobiose, a beta-1,4-linked glucose disaccharide, maltose (the alpha-1,4-linked isomer) and other related compounds with alkali has been shown to generate low yields of the desired material along with D,L-2,4-dihydroxybutanoic acid, glycolic acid, isosaccharinic acids, ketones, diketones, glyceric acids and a myriad of other degradation and condensation products (Corbett, W. M., et al., J. Chem. Soc., 1431–1435 (1955); Green, J. W., J. Amer. Chem. Soc. 78:1894–1897 (1956); and Rowell, R. M., et al., Carbohydr. Res. 11:17–25 (1969)). Starch and cellulose also yield similar compounds in what is known as the "peeling reaction". This process was generally thought to have no synthetic potential. Most of the products formed in these reactions are formed from the intermediate dicarbonyl (diulose) compound F shown in FIG. 1 according to a mechanism proposed by Isbell (Isbell, H. S., J. Res. Natl. Bur. Stand., 29:227 (1942)). The dicarbonyl compound F is rapidly attacked by alkali to yield a tarry mixture and the formation of 3,4-dihydroxybutanoic acid (1) and glycolic acid (4) as shown in FIG. 1 in low yields and is slow and oxygen-dependent.

Alkaline hydrogen peroxide rapidly cleaves diketones to give carboxylic acids and treatment of diuloses and other carbohydrates with hydrogen peroxide in this manner has been described (Moody, G. J., Advances in Carbohydr. Chem. 19:149–180 (1964)). The reference does not describe the use of hydrogen peroxide to cleave a glucose source containing a 1,4-glucose linkage. Earlier work on the oxidation of maltose (Glattfield, J. W. E., et al., J. Amer. Chem. Soc. 40:973 (1918) using base and hydrogen peroxide yielded no 3,4-dihydroxybutanoic acid but gave glycolic acid, arabonic acid, D-erythronic acid, oxalic acid and formic acid. In this work, the reaction was conducted for a very prolonged period (13 days) at room temperature followed by an undefined period at 50° C. The molar proportions of base and hydrogen peroxide were both 8 to 9 fold of the sugar proportion. These conditions cause complete conversion of product to formic acid.

U.S. Pat. Nos. 5,292,939, 5,319,110 and 5,374,773 to the present inventor describe a significant improvement in the preparation of 3,4-dihydroxybutanoic acid and salts from a D- or L-hexose source using a base and a peroxide oxidizing agent. The preparation of the lactones is also described. The purpose of the present invention is to improve upon these processes.

The methods described for the preparation and isolation of optically active 3-hydroxy-γ-butyrolactone by the alkaline oxidation of 4-linked hexoses have several drawbacks that limit their utility in commercial processes. One of the major limitation in the oxidation is that very low concentrations of peroxide and hydroxide and are typically used (Hollingsworth, R., U.S. Pat. Nos. 5,292,939; 5,319,110 and 5,374,773; Hollingsworth, R., J. Org. Chem. 64:7633–7634 (1999); and Huang, G. and R. I. Hollingsworth, Tetrahedron 54:1355–1360 (1998)). This limits the concentration of carbohydrate substrate that can be transformed to product to 0.02M or less. Because of this, the throughput of a commercial manufacturing system is severely limited. The concentrations of peroxide and hydroxide cannot be increased without the onset of unfavorable side reactions.

Another serious limitation is the necessity of removing all of the water from the acidified reaction mixture to effect lactonization of the 3,4-dihydroxy acid to the corresponding 3-hydroxy-γ-butyrolactone product. It is estimated that 80% of the time spent in water removal is used in removing the last 20%. The time for water removal on a batch size of over 3,000 gallons is several days. There is also a tendency for the undesired acid catalyzed dehydration of the lactone to occur leading to the formation of 2(5H)-furanone. Another complication is that the syrup formed in the complete water removal stage is often too viscous to allow proper agitation. This leads to further dehydration because of local overheating. Yet another complication is the requirement for six or more extractions of the syrup with a suitable organic solvent for acceptable recovery of the lactone product. The resistance of the syrup to flow and the large number of extractions needed do not allow the implementation of a process where the reaction mixture can be concentrated and extracted in a continuous fashion. These drawbacks present a significant barrier to the efficient commercial utilization of this route to these important hydroxy acids and their corresponding lactones.

3,4-Dihydroxybutanoic and is a valuable chiral building block and the general strategies for obtaining it and its derivatives hinge upon the development of enzymatic systems utilizing beta-ketoesters as substrates (Nakamura, N., et al., Tetrahedron Letters, 30:2245–2246 (1989); Zhou, B., et al., J. Amer. Chem. Soc., 105:5925–5926 (1983); and Nakamura, N., et al., Tetrahedron Letters, 31:267–270 (1990)).

A chiral chemistry platform has been developed based on optically active 3,4-dihydroxybutyric acids and their gamma lactones. They allow access to other compounds ranging from alcohols, amines, halides, acids, esters, epoxides, acetals, tetrahydrofurans, pyrolidines, amides, nitriles and acid halides through much more complex structures in a stereospecific method. These compounds are important intermediates in the synthesis of a variety of chiral drug substances ranging from antiviral through broad spectrum antibiotics to cholesterol lowering drugs and drugs used for diabetes management. These uses are well documented in the literature (Corey, E. J., et al., J. Amer. Chem. Soc. 100 1942–1943 (1978); Uchikawa, O., et al., Bull. Chem. Soc. Jpn. 61 2025–2029 (1988); Hayashi, H., et al., J. Amer. Chem. Soc. 95 8749–8757 (1973); Danklmaier, J., et al., Liebigs. Ann. Chem. 1149–1153 (1988); Mori, Y., et al., Tetrahedron Letts. 29 5419–5422 (1988); Shieh, H. M., et al., Tetrahedron Letts 23 4643–4646 (1982); Mori, K., et al., Tetrahedron Letts 29 5423–5426 (1988); and Saito, S., et al., Chem. Letts 1389–1392 (1984)). They include the preparation of compounds such as eicosanoids (Corey, E. J., et al., J. Amer. Chem. Soc. 100 1942–1943 (1978)), modified nucleic acid bases (Hayashi, H., et al., J. Amer. Chem. Soc. 95 8749–8757 (1973)), the polyol function of macrolide antibiotics (Mori, Y., et al., Tetrahedron Letts. 29 5419–5422 (1988)), and (−) aplysistatin, an anti-cancer agent (Shieh, H. M., et al., Tetrahedron Letts 23 4643–4646 (1982)). The facile preparation of beta-lactams (an entire family of antibiotics) is also possible as is the preparation of the lactone ring of cholesterol lowering drugs such as Atorvastatin and Mevacor. More recently its use has been expanded into a variety of other areas, one important example of which is the synthesis of chiral substituted azetidinones (β-lactams) by the Schering Plough group (Wu, G., et al., J. Org. Chem. 64 3714–3718 (1999)). There are several other recent reports on the exploitation of this lactone in the pharmaceutical arena (Song, J., et al., J. Amer. Chem. Soc 121 1851–1861 (1999); Wang, G., et al., J. Org. Chem. 64 1036–1038 (1999); Huang, G., et al., Tetrahedron Asymmetry 9 4113–4115 (1999); and Wang, G., et al., Tetrahedron Assym. 10 1895–1901 (1999)). These include the transformation of the 4-carbon synthon to optically active 3-carbon molecules which immediately open up the possibility of addressing the synthesis of a much wider range of drugs including the β-blockers and antivirals such as Cidofovir (Wang, G., et al., J. Org. Chem. 64 1036–1038 (1999)). The direct preparation of these optically active hydroxy acids and lactones by the alkaline oxidation of carbohydrates in a form that is directly usable for these further transformations is a significant advance in synthetic chemistry especially in the areas of drug discovery, synthesis and manufacture. Another important aspect of the use of these hydroxy acids and lactones is that the integrity of the chiral centers can be maintained through the transformations. The oxidation of carbohydrates is especially important because substituted D-sugars give the (S) dihydroxy acid, and the corresponding y-lactone and L-sugars give the mirror image R-compounds.

OBJECTS

It is therefore an object of the present invention to provide an improved process for preparing optically active 3,4-dihydroxybutanoic acid from hexose sources and to a process for producing and isolating lactones therefrom. It is further an object of the present invention to provide improved processes which are relatively easy to perform and are economical. These and other objects will become increasingly apparent by reference to the following description and the drawings.

IN THE DRAWINGS

SUMMARY OF THE INVENTION

Figure 1:
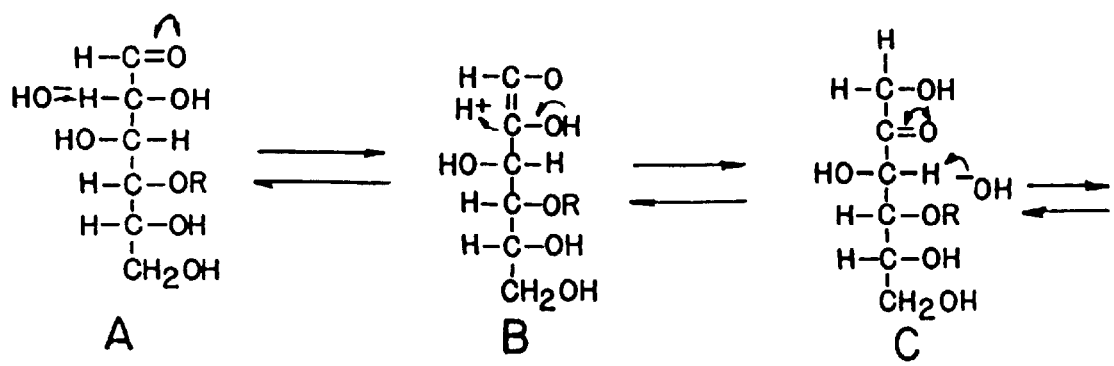
FIG. 1 shows the mechanism of alkaline peroxide degradation of a 4-linked glucose.
Figure 1:
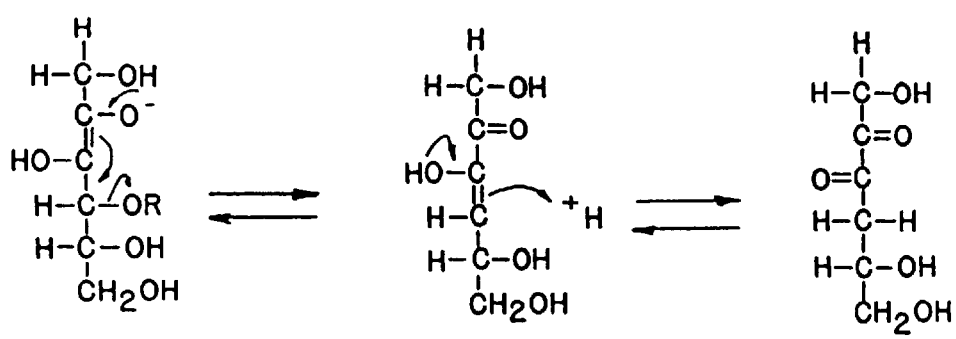
Figure 1:
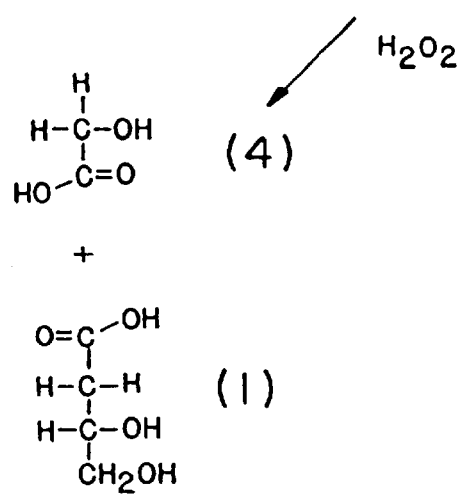

The present invention relates to a process for the preparation of a lactone which comprises:

(a) reacting in a reaction mixture 3,4-dihydroxybutyric acid (HBA) or salt thereof in an aqueous solution of a base selected from the group consisting of an alkali metal hydroxide, an alkaline earth metal hydroxide and mixtures thereof with a strong acid in an amount between about 0.9 and 3 equivalents based upon the base by addition of the acid to the aqueous solution of the base over a period of time at a temperature of less than about 60° C.;

(b) mixing a polar organic solvent and a compound selected from the group consisting of an amine, an ammonium salt and mixtures thereof into the reaction mixture in an amount between about 0.9 and 3 equivalents based upon the base to form an ammonium salt of the HBA in the polar organic solvent; and (c) separating the polar organic solvent containing the ammonium salt of the HBA from the reaction mixture; and (d) heating the ammonium salt of the HBA in the polar organic solvent to remove the organic solvent and to form the lactone. Preferably the organic solvent in step (b) is water insoluble under the conditions used in the process.

The present invention also relates to a process for the preparation of a lactone which comprises:

(a) reacting 3,4-dihydroxybutyric acid (HBA) or a salt thereof in an aqueous solution of a base selected from the group consisting of alkali metal hydroxide, an alkaline earth metal hydroxide and mixtures thereof with a strong acid in an amount between about 0.9 and 2 equivalents based upon the base by addition of the acid to the aqueous solution of the base over time at a temperature which is maintained at or less than about 60° C.;

(b) mixing a water miscible polar organic solvent and an amine containing compound selected from the group consisting of lower monoalkyl amine, a dilower alkyl amine, a trilower alkyl amine, an ammonium salt and mixtures thereof into the reaction mixture in an amount between 0.9 and 3 equivalents based upon the base to form an ammonium salt of the HBA in the reaction mixture;

(c) separating the organic solvent containing the ammonium salt of HBA from the reaction mixture; and (d) heating the ammonium salt of the HBA in the water miscible organic solvent to remove the organic solvent and to form the lactone.

The present invention also relates to an improved process for the conversion of a D- or L-hexose sugar source into 3,4-dihydroxybutyric acid and glycolic acid as salts by reacting in a reaction mixture the hexose source with a base selected from the group consisting of an alkali metal hydroxide, an alkaline earth metal hydroxide and mixtures thereof and a peroxide oxidizing agent until 3,4-dihydroxybutyric acid and glycolic acid as the salts are formed as essentially the only products, wherein the total peroxide and the base used are present in a range up to a 4 molar excess over the D- or L-hexose and wherein the substituted D- or L-hexose is between about 0.05 to 80% by weight per volume of the reaction mixture, which comprises: adding the peroxide and the base to the reaction mixture over a period of time which is less than about 5 hours so that at any time during the reaction mixture the concentration of the peroxide oxidizing agent and the base in the reaction mixture is less than 0.02M and with heating at a temperature between about 25° C. and 80° C. to produce the salts. Preferably the D- or L-hexose source is a glucose source.

The present invention also relates to a process for the conversion of a 4–0-substituted D- or L-hexose source to an internal cyclic ester which comprises: reacting in a reaction mixture the D- or L-hexose with a base selected from the group consisting of an alkali metal hydroxide and an alkaline earth metal hydroxide and a peroxide oxidizing agent until 3,4-dihydroxybutyric acid and glycolic acid as salts from the D- or L-hexose source are formed as essentially the only products, wherein the peroxide oxidizing agent and the base are present in a range up to a 4 molar excess over the D- or L-hexose and wherein the D- or L-hexose source is between about 0.05 to 80% by weight per volume of the reaction mixture by adding the peroxide oxidizing agent and the base to the reaction mixture over a period of time which is less than about 5 hours so that at any time during the reaction the concentration of the peroxide oxidizing agent and the base in the reaction mixture is less than 0.02M with heating at a temperature between about 25° C. and 80° C. to form the salts; and acidifying the reaction mixture to produce an internal cyclic ester.

The present invention also relates to a process for the conversion of a D- or L-hexose source to a 3,4-dihydroxybutanoic acid as the salt which comprises: reacting in a reaction mixture the D- or L-hexose with a first base selected from the group consisting of an alkali metal hydroxide, an alkaline earth metal hydroxide and mixtures thereof and a peroxide oxidizing agent until 3,4-dihydroxybutyric acid and glycolic acid as the salts from the D- or L-hexose source are formed as essentially the only products, wherein the peroxide oxidizing agent and the base are added to a total amount in a range up to a 4 molar excess over the D- or L-hexose and wherein the D- or L-hexose source is between about 0.05 to 80% by weight per volume of the reaction mixture by adding the peroxide oxidizing agent and the base to the reaction mixture over a period of time which is less than about 3 hours so that at any time during the reaction the concentration of each in the reaction mixture is less than 0.02M with heating at a temperature between about 25° C. and 80° C. to form the salts; acidifying the reaction mixture to produce an internal cyclic ester; and heating the internal cyclic ester with a second base selected from the group consisting of an alkali metal hydroxide, an alkaline earth metal hydroxide and mixtures thereof to produce the 3,4-dihydroxybutanoic acid as the salt.

The preferred reactions are shown in Schemes I and II as follows:

I Glucose Source + alkali metal hydroxide + H$_2$O$_2$ $\xrightarrow[\text{24 hours}]{70° \text{C.}}$

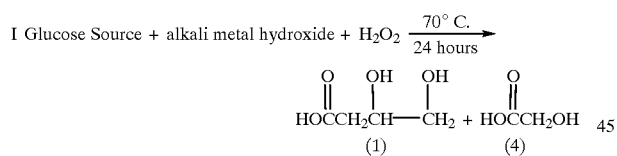

as the alkali metal salt

II (1) + acid $\xrightarrow{\text{heat}}$ 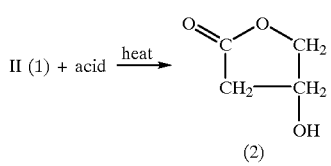

The preferred 4–0-substituted D- or L-hexose sugar is maltose, lactose, cellobiose, cello-oligosaccharides and maltodextrins. The hexoses in the hexose source can be any hexose such as galactose, mannose, glucose and the like. These sugars will produce the 3,4-dihydroxybutyric acid by the process of the present invention. Other sources are starch, starch hydrolysates and cellulose. Both cellulose and starch are among the most abundant materials on earth. The process of the present invention transforms these and similar abundant, renewable resources to otherwise inaccessible intermediates which can be used in the pharmaceutical, chemical and polymer industries and reduce our dependence on petrochemicals.

The peroxide oxidizing agent can be any peroxide which will produce the 3,4-dihydroxybutyric acid. These include alkaline earth metal peroxides such as barium peroxide, the alkali metal peroxides such as sodium peroxide and hydrogen peroxide, which is preferred. The selection of the peroxide is within the skill of the art.

The base is selected from alkali metal and alkaline earth metal peroxides. These include zinc hydroxide, calcium hydroxide (lime), potassium hydroxide, sodium hydroxide and the like. The selection of the base is with the skill of the art.

Preferably sodium hydroxide or potassium hydroxide and hydrogen peroxide are used in molar equivalents between 1 to 2 fold of the total 4-O-linked hexose. A molar equivalent up to 4 fold can be used, but with increasing degradation of the desired product. The hexose source is preferably at least about 0.05 percent up to about 80% by weight per volume of the reaction mixture. The reaction of the base with the hexose source is conducted for less than about five (5) hours. The concentration of base in the reaction mixture is not allowed to exceed 0.02M during the addition. The reaction is conducted at a temperature range between about 250° and 80° C. The base concentration is preferably between about 0.005M and 0.02M. The peroxide oxidizing agent is preferably between about 0.005M and 0.02M.

On acidification of the alkali metal salt of 3,4-dihydroxybutyric acid, (1) undergoes spontaneous cyclization to yield the gamma-lactone (2) according to the process of the present invention as follows:

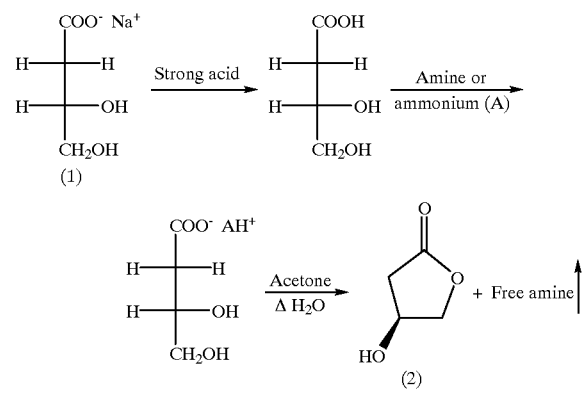

The lactone (2) is dehydrated, on heating in the presence of acid, to yield an unsaturated lactone. Treatment of the lactone (2) with hydrogen bromide in acetic acid in the presence of ethanol should readily yield (S)-4-bromo-3-hydroxybutanoic acid ethyl ester, the key fragment in our chiral 3-hydroxy fatty acid syntheses.

The lactone can be separated from the by-products formed by extraction into an organic solvent selected from the group consisting of ethyl acetate, methylethyl ketone, 2-propanol, 1-propanol, t-butanol, 2-butanol, tetrahydrofuran and 1,4-dioxane. Any organic solvent in which the lactone is soluble can be used. The solvent of choice for the extraction is ethyl acetate, although tetrahydrofuran, 1,4-dioxide, methyl ethyl ketone, acetone, n-propanol, butanols or acetone can be used. Polar solvents tend to extract more degraded carbohydrate impurities.

An alkali metal or alkaline earth metal base can be used to convert the internal cyclic ester (lactone) to the 3,4- dihydroxybutanoic acid (HBA) salt. This step is usually unnecessary since the salt of the HBA salt is isolated prior to the formation of the lactone.

DESCRIPTION OF PREFERRED EMBODIMENTS

Materials and Methods

In the improved oxidation process the concentration of the substrate carbohydrates and hence the throughput of the process can be increased several fold over the older process by adding the hydrogen peroxide and sodium hydroxide simultaneously using matched burettes or pumps at such a rate that the rate of their consumption to form products results in an instantaneous concentration of these reagents that is below the required 0.02M limit for efficient conversion to product. In a preferred oxidation, maltose was dissolved in water 500 ml and the mixture heated to 60° C. Hydrogen peroxide and sodium hydroxide were added at the same rate over a 5 hour period. Heating was continued for a further 1.5 hours after which time NMR spectroscopy indicated complete conversion to the desired 3,4-dihydroxybutyric acid as the salts.

The solvent of choice for the extraction of the lactone is ethyl acetate although tetrahydrofuran, 1,4-dioxane, methyl ethyl ketone, acetone, n-propanol, butanols or acetone can be used. Polar solvents tend to extract more degraded carbohydrate impurities.

In the improved isolation procedure for the hydroxylactone, 1 equivalent of sulfuric acid (relative to the number of equivalents of sodium hydroxide used) was added to the reaction mixture of Example 1 with the temperature not being allowed to exceed 25° C. The solution is reduced to ¼ the original volume and acetone in an amount equal to 3 times the remaining volume and containing 1 equivalent of triethylamine (relative to the amount of sodium hydroxide added) was added and the mixture agitated for 30 minutes. Toluene, 2-propanol and ethyl acetate were also used. Very little product was extracted into toluene. Extraction into 2-propanol was excellent but the quality of the product was low. There was good (~50% of the product) extraction into ethyl acetate but the quality of the material was excellent as indicated by the absence of extraneous signals due to degraded sugars between 3.0 and 4.0 ppm in the proton NMR spectra. The phases were allowed to separate and the upper acetone layer was recovered. Concentrating under vacuum at 45° C. yielded a syrup containing the desired 3-hydroxy lactone, some triethylammonium sulfate, and the triethylammonium salt of glycolic acid (in the case of 4-linked hexoses).

The 3-hydroxy lactone can be isolated by several methods:

(1) Re-dissolution of the mixture in ethyl acetate and washing with 10% by volume of a saturated solution of sodium acetate which was preferred. This exchanges sulfate and glycolate with acetate. Concentration of the ethyl acetate layer give a product suitable for further transformations.
(2) All of the charged species can be removed by passage through a mixed bed resin or by sequential passage through a cation exchange (H form) and an anion exchange (OH, acetate or formate) resin.
(3) The anions alone can be removed by exchanging with formate or acetate by ion exchange. Triethylammonium formate is eliminated from the solution during the concentration.
(4) The charged impurities can be removed by electrodialysis.
(5) The less basic triethylamine can be deprotonated by a stronger amine base such as triethanolamine that can be separated from the mixture by extraction with water due to its higher polarity.
(6) The more volatile triethylamine can be removed from the reaction mixture by displacement with a less volatile amine base such as triethanolamine.

The concentrations can be scaled linearly. In this oxidation method any 4-linked hexose can be used. At this stage the dihydroxy acid can be isolated directly by anion exchange chromatography. Alternatively, acidification, concentration and extraction of the 3-hydroxylactone at this stage with an organic solvent affords material of a purity that is suitable for direct transformation to the classes of intermediates mentioned above.

The process of the present invention circumvented several basic problems with the earlier Hollingsworth isolation process and give material that can be transformed directly to the classes of intermediates described. The problems were as follows:

(1) In the earlier process, all of the water had to be removed to effect cyclization (about 80% of the concentration time is used to remove the last 20% of water).
(2) The problems with viscosity in the earlier process were avoided because all of the water is not removed in the improved process.
(3) In the earlier process, heating in acid lead to coloration and to dehydration to form a furanone. This does not occur in the improved process of the present invention.
(4) Six extractions with ethyl acetate were no longer needed as with the earlier process.
(5) Acetone can be used instead of ethyl acetate as in the earlier process which is expensive.
(6) The rapid phase equilibration and solvent separation during the extraction are such that rapid and continuous solvent-solvent extraction can be used in the improved process.

NMR spectra were recorded on a Varian GEMINI spectrometer operating at 300 MHz for proton frequencies. Chemical shifts are given relative to external TMS. IR spectra were recorded on a NICOLET 710 spectrometer in chloroform solution.

EXAMPLE 1

In a preferred oxidation, maltose (125 g) was dissolved in water 500 ml and the mixture heated to 60° C. Hydrogen peroxide (37.5 ml diluted to 100 ml with water) and sodium hydroxide (31.25 g diluted to 100 ml with water) were added at the same rate over a 5 hour period. Heating was continued for a further 1.5 hours after which time NMR spectroscopy indicated complete conversion to the desired dihydroxy acid. At the end of the alkaline oxidation process, 1 equivalent of sulfuric acid (relative to the number of equivalents of sodium hydroxide used) was added with the temperature not being allowed to exceed 25° C. The solution was reduced to ¼ the original volume and split into 5 equal amounts for production of the lactone as in Examples 4 to 8.

EXAMPLE 2

Isolation using acetone: An amount of acetone equal to 3 times the reaction mixture and containing 1 equivalent of triethylamine (relative to the amount of sodium ion in the reaction mixture) was added and the mixture agitated for 30 minutes. The phases are allowed to separate and the upper acetone layer containing the dihydroxybutyric acid as its triethylammonium salt was recovered. Concentrating under vacuum at 45° C. effects cyclization and yielded a syrup containing the desired 3-hydroxy lactone, some triethylammonium sulfate, and the triethylammonium salt of glycolic acid. NMR spectroscopy indicated that none of the desired dihydroxybutyric acid product remained in the aqueous layer.

EXAMPLE 3

Isolation using ethyl acetate: An amount of ethyl acetate equal to 3 times the reaction mixture and containing 1 equivalent of triethylamine (relative to the amount of sodium ion in the reaction mixture) was added and the mixture agitated for 30 minutes. The phases were allowed to separate and the upper ethyl acetate layer containing the dihydroxybutyric acid as its triethylammonium salt was recovered. The lower aqueous layer was extracted another 2 times with ethyl acetate. Concentrating the combined ethyl acetate layers under vacuum at 45° C. effected cyclization and yielded a syrup containing the desired 3-hydroxy lactone with only small amounts of triethylammonium sulfate, and the triethylammonium salt of gycolic acid. NMR spectroscopy indicated that less than 10% of the desired dihydroxybutyric acid product remained in the aqueous layer.

EXAMPLE 4

Isolation using ethyl methyl ketone: An amount of ethyl methyl ketone equal to 3 times the reaction mixture and containing 1 equivalent of triethylamine (relative to the amount of sodium ion in the reaction mixture) was added and the mixture agitated for 30 minutes. The phases were allowed to separate and the upper ethyl methyl ketone layer containing the dihydroxybutyric acid as its triethylammonium salt was recovered. The lower aqueous layer was extracted another 2 times with ethyl methyl ketone. Concentrating the combined ethyl methyl ketone layers under vacuum at 45° C. effects cyclization and yielded a syrup containing the desired 3-hydroxy lactone, and less than 50 mole % of triethylammonium sulfate, and the triethylammonium salt of glycolic acid. NMR spectroscopy indicated that less than 5% of the desired dihydroxybutyric acid product remained in the aqueous layer.

EXAMPLE 5

Isolation using n-propanol: An amount of n-propanol equal to 3 times the reaction mixture and containing 1 equivalent of triethylamine (relative to the amount of sodium ion in the reaction mixture) was added and the mixture agitated for 30 minutes. The phases were allowed to separate and the upper n-propanol layer containing the dihydroxybutyric acid as its triethylammonium salt was recovered. Concentrating the n-propanol layer under vacuum at 45° C. effected cyclization and yielded a syrup containing the desired 3-hydroxy lactone, and about 80 mole % of triethylammonium sulfate, and the triethylammonium salt of glycolic acid. NMR spectroscopy indicated that none of the desired dihydroxybutyric acid product remained in the aqueous layer which was substantially reduced in volume because of loss of water to the n-propanol layer. The n-propanol layer also contained appreciable amounts of carbohydrate material.

EXAMPLE 6

Isolation using tetrahydrofuran: An amount of tetrahydrofuran equal to 3 times the reaction mixture and containing 1 equivalent of triethylamine (relative to the amount mount of sodium ion in the reaction mixture) was added and the mixture agitated for 30 minutes. The phases were allowed to separate and the upper tetrahydrofuran layer containing the dihydroxybutyric acid as its triethylammonium salt was recovered. Concentrating the tetrahydrofuran under vacuum at 45° C. effected cyclization and yielded a syrup containing the desired 3-hydroxy lactone, and about 60 mole % of triethylammonium sulfate, and the triethylammonium salt of glycolic acid. NMR spectroscopy indicated that none of the desired dihydroxybutyric acid product remained in the aqueous layer which was substantially reduced in volume because of loss of water to the tetrahydrofuran layer. The tetrahydrofuran layer also contained appreciable amounts of carbohydrate material.

EXAMPLE 9

60 grams of a maltodextrin mixture (Staley "Stardry 10" maltodextrin) was dissolved in water (300 ml) and the solution was heated to 60 degrees centigrade. Sodium hydroxide (40 grams) dissolved in 300 ml of water and hydrogen peroxide (60 grams) dissolved in 300 ml of water were added to the heated solution over a 6 hour period. Heating was continued for a further 3 hours after the addition was completed. At this stage NMR spectroscopy indicated complete conversion of the product maltodextrins to glycolic acid and (S)-3,4-dihydroxy-γ-butyrolactone. The optical purity of the product by gas chromatography using a Supelco cyclodextrin bonded column after converting a small sample to the γ-lactone was >99.9%. The conversion to product was >90%.

EXAMPLE 10

Figure 2:
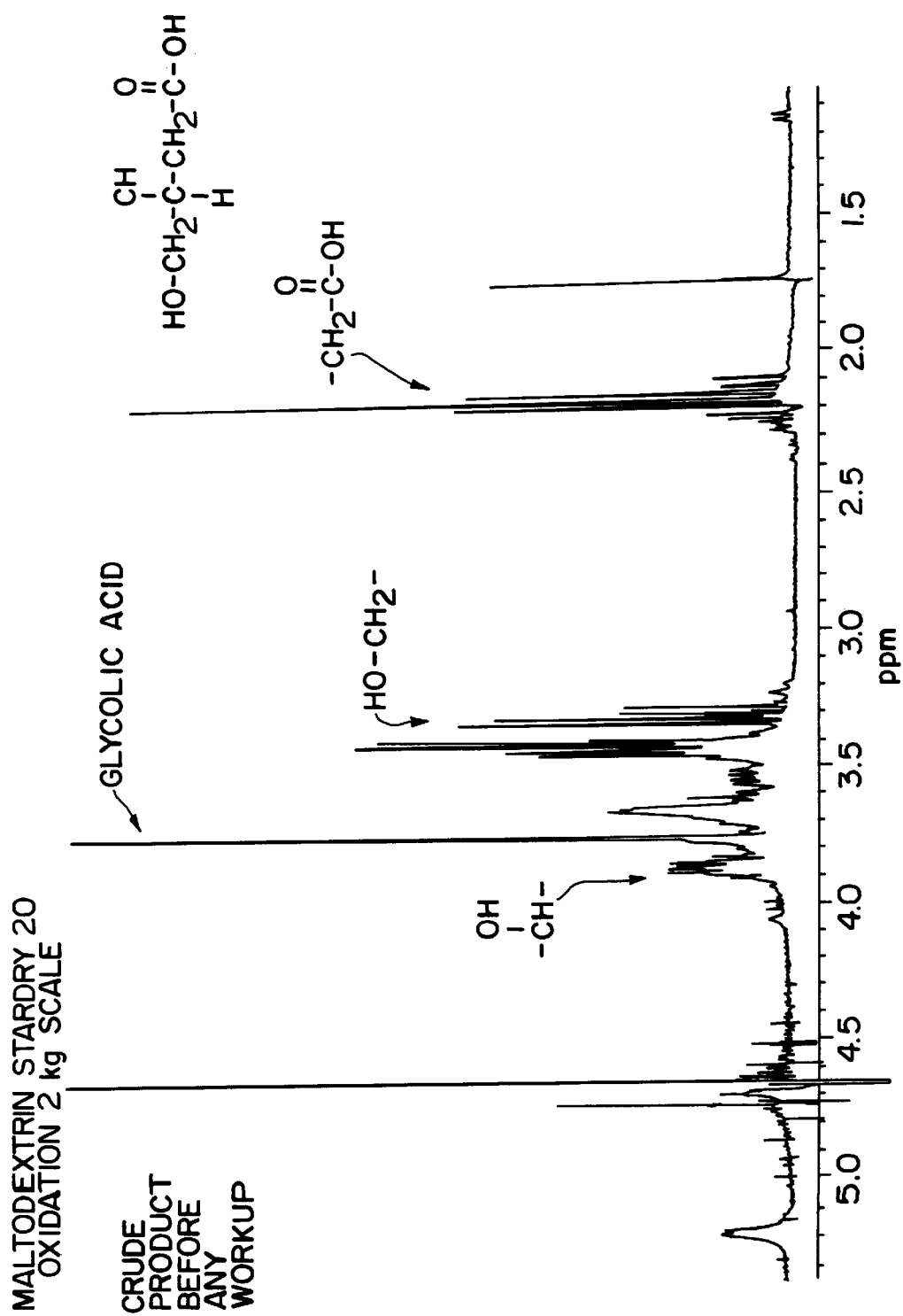
FIG. 2 shows the NMR spectroscopy for the products of Example 10.

Maltodextrin (Staley "Stardry 20) (2000 g, 12.3 moles glucose equivalents) was dissolved in 3 liters of water and the solution heated to 60 degrees centigrade. Sodium hydroxide (988 grams, 24.6 moles dissolved in and diluted to 2 liters with water) and hydrogen peroxide (1.4 liters of a 30% solution=418 g $H_2O_2$=12.3 moles diluted to 2 liters) were pumped in over a 6 hour period. Heating was continued for a further 3 hours. At this stage NMR spectroscopy (FIG. 2) indicated complete conversion of the product maltodextrins to glycolic acid and (S)-3,4-dihydroxy-γ-butyrolactone. The optical purity of the product by gas chromatography using a Supelco cyclodextrin bonded column after converting a small sample to the y-lactone was >99.9%. The conversion to product was >90%.

It is intended that the foregoing description be only illustrative of the present invention and that the present invention be limited only by the hereinafter appended claims.

I claim:

1. A process for the preparation of a lactone which comprises:
    (a) reacting in a reaction mixture the 3,4-dihydroxybutyric acid (HBA) or salt thereof in an aqueous solution of a base selected from the group consisting of an alkali metal hydroxide, an alkaline earth metal hydroxide and mixtures thereof with a strong acid in an amount between about 0.9 and 3 equivalents based upon the base by addition of the acid to the aqueous solution of the base over a period of time at a temperature of less than about 60° C.;
    (b) mixing a polar organic solvent and an amine containing compound selected from the group consisting of an amine, an ammonium salt and mixtures thereof into the reaction mixture in an amount between about 0.9 and 3 equivalents based upon the base to form an ammonium salt of the HBA in the polar organic solvent; and (c) separating the polar organic solvent containing the ammonium salt of the HBA from the reaction mixture; and (d) heating the ammonium salt of the HBA in the polar organic solvent of the HBA to form the lactone.

2. A process for the preparation of a lactone which comprises:

(a) reacting 3,4-dihydroxybutyric acid (HBA) or a salt thereof in an aqueous solution of a base selected from the group consisting of alkali metal hydroxide, an alkaline earth metal hydroxide and mixtures thereof with a strong acid in an amount between about 0.9 and 2 equivalents based upon the base by addition of the acid to the aqueous solution of the base over time at a temperature which is maintained at or less than about 60° C.;

(b) mixing a water miscible polar organic solvent and an amine containing compound selected from the group consisting of lower monoalkyl amine, a dilower alkyl amine, a trilower alkyl amine, an ammonium salt and mixtures thereof into the reaction mixture in an amount between 0.9 and 3 equivalents based upon the base to form an ammonium salt of the HBA in the reaction mixture;

(c) separating the organic solvent containing the ammonium salt of HBA from the reaction mixture;

(d) heating the ammonium salt of the HBA in the water miscible organic solvent to remove the organic solvent and to form the lactone.

3. The process of claim 2 wherein the alkali metal hydroxide is sodium hydroxide.

4. The process of claim 2 wherein the strong acid is sulfuric acid is between about 0.9 and 1 equivalents.

5. The process of claim 2 wherein the organic solvent is acetone.

6. The process of claim 2 wherein the amine is triethylamine.

7. The process of claim 2 wherein temperature in step (a) is less than about 25° C.

8. The process of claim 2 wherein a temperature for the mixing in step (b) is about 45° C.

9. The process of claim 2 wherein by-products which can be present in the lactone which is formed in step (d) are removed from the lactone by mixing the lactone with a second organic solvent selected from the group consisting of ethyl acetate, methyl ethyl ketone, 2-propanol 1, 1-propanol 1, butanol, t-butanol, 3-butanol, 2-butanol, tetrahydrofuran and 1,4-dioxane and an aqueous solution of an alkali metal acetate and wherein the lactone is separated from the water in the solvent which is then removed to provide the lactone.

10. The process of claim 2 wherein by-products which are ionic with the lactone which is formed in step (d) are removed from the lactone upon being passed through an anion and cation exchange resin.

11. The process of claim 2 wherein in step (d) by-products which are ionic with the lactone which is formed in step (d) are exchanged by ion exchange with a cation which renders the by-products water soluble and which are then removed from the lactone with water.

12. The process of claim 2 wherein by-products which are with the lactone which is formed in step (d) are removed by electrodialysis.

13. The process of claim 2 wherein byproducts which are with amine containing compound in the lactone which is formed in step (d) is removed from the lactone by introducing a water soluble amine which reacts with the compound to form a water soluble product which is removed with water.

14. The process of claim 2 wherein any remaining of the amine containing compound is removed from the lactone by being displaced by triethyl amine which is then removed with water from the lactone.

15. In a process for the conversion of a D- or L-hexose sugar source into 3,4-dihydroxybutyric acid and glycolic acid as salts by reacting in a reaction mixture the D- or L-hexose with a base selected from the group consisting of an alkali metal hydroxide, an alkaline earth metal hydroxide and mixtures thereof and a peroxide oxidizing agent until 3,4-dihydroxybutyric acid salt and glycolic acid or formic acid are formed as essentially the only products, wherein the total peroxide oxidizing agent and the base used are in a range up to a 4 molar excess over the D- or L-hexose and wherein the D- or L-hexose is between about 0.05 to 80% by weight per volume of the reaction mixture, the improvement which comprises:

matched adding of concentrations of the peroxide and the base simultaneously into the reaction mixture over a period of time which is less than about 5 hours so that at any time during the reaction mixture the concentration of the peroxide oxidizing agent and the base in the reaction mixture is less than 0.02M and with heating at a temperature between about 25° C. and 80° C. to produce the salts.

16. The process of claim 15 wherein the sugar source is selected from the group consisting of maltose, lactose, cellobiose, cell-oligosaccharides and maltodextrins.

17. The process of claim 15 wherein the sugar source is selected from the group consisting of starch and starch hydrolysates.

18. The process of claim 15 wherein the D-hexose source is cellulose.

19. The process of claim 15 wherein the base is between about 0.005M and 0.02M and wherein the peroxide oxidizing agent is between about 0.005M and 0.02M in the reaction mixture.

20. The process of claim 15 wherein the peroxide oxidizing agent is selected from the group consisting of alkali metal peroxides, alkaline earth metal peroxides and hydrogen peroxide.

21. The process of claim 15 wherein the 3,4-dihydroxybutyric acid is separated from the reaction mixture.

22. In a process for the conversion of a D- or L-glucose into 3,4-dihydroxybutyric acid and glycolic acid as salts by reacting in a reaction mixture the D- or L-glucose source with a base selected from the group consisting of an alkali metal hydroxide, an alkaline earth metal hydroxide and mixtures thereof and a peroxide oxidizing agent until 3,4-dihydroxybutyric acid and glycolic acid as salts are formed, wherein the peroxide oxidizing agent and the base are present in a range up to a 4 molar excess over the D- or L-glucose and wherein the D- or L-glucose source is between about 0.05 to 80% by weight per volume of the reaction mixture, the improvement which comprises:

matched adding of concentrations of the peroxide and the base simultaneously into the reaction mixture over a period of time which is less than about 5 hours so that at any time during the reaction mixture the concentration of the peroxide oxidizing agent and the base in the reaction mixture is less than 0.02M with heating at a temperature between about 25° C. and 80° C. to produce the salts.

23. The process of claim 22 wherein the glucose source is as the D-glucose source and the 3,4-dihydroxybutyric acid is (S)-3,4-dihydroxybutanoic acid.

24. The process of claim 22 wherein the glucose source is selected from the group consisting of lactose, maltose, hexose and maltodextrins.

25. The process of claim 22 wherein the glucose source is selected from the group consisting of starch and starch hydrolysates.

26. The process of claim 22 wherein the glucose source is cellulose.

27. The process of claim 22 where the glucose source is lactose.

28. The process of claim 22 wherein the base is sodium hydroxide, wherein the sodium hydroxide is between about 0.005M and 0.02M and wherein the peroxide oxidizing agent is between about 0.005M and 0.02M.

29. The process of claim 22 wherein the glycolic acid is separated from the reaction mixture by distillation.

30. The process of claim 23, wherein the reaction is conducted for at least about 2 hours.

31. The process of claim 30 wherein the reaction is conducted at about 60° C. for between about 3 and 5 hours.

32. The process of claim 10 wherein the 3,4-dihydroxybutyric acid as the salt is separated from the reaction mixture.

33. A process for the conversion of a D- or L-hexose source to an internal cyclic ester which comprises:
(a) reacting in a reaction mixture the D- or L-hexose source with a base selected from the group consisting of an alkali metal hydroxide, an alkaline earth metal hydroxide and mixtures thereof and a peroxide oxidizing agent until 3,4-dihydroxybutyric acid and glycolic acid as salts from the D- or L-hexose source are formed as essentially the only products, wherein the peroxide oxidizing agent and the base are present in a range up to a 4 molar excess over the D- or L-hexose and wherein the D- or L-hexose source is between about 0.05 to 80% by weight per volume of the reaction mixture by matched adding of concentrations of the peroxide oxidizing agent and the base simultaneously into the reaction mixture over a period of time which is less than about 5 hours so that at any time during the reaction the concentration of the peroxide oxidizing agent and the base in the reaction mixture is less than 0.02M with heating at a temperature between about 25° C. and 80° C. to form the salts; and
(b) acidifying the reaction mixture to produce an internal cyclic ester.

34. The process of claim 33 wherein the internal cyclic ester is a lactone.

35. The process of claim 33 wherein the internal cyclic ester is removed from the reaction mixture by distillation.

36. The process of claim 33 wherein the 3,4-dihydroxybutyric acid is (S)-3,4-dihydroxybutanoic acid and wherein the reaction mixture is acidified and heated in step (b) to produce (S)-3,4-dihydroxybutanoic acid gamma-lactone as the internal cyclic ester.

37. The process of claim 36 wherein the gamma lactone is converted to 2(5H)-furanone by distillation of the reaction mixture to produce the 2(5H)-furanone as a distillate.

38. The process of claim 36 wherein the gamma-lactone is heated with a second base selected from the group consisting of an alkali metal hydroxide and an alkaline earth metal hydroxide to produce a 3,4-dihydroxybutanoic acid salt.

39. The process of claim 38 wherein the alkali metal hydroxide is sodium hydroxide and the salts are the sodium salts.

40. The process of claim 33 wherein the D- or L-hexose source is a glucose source.

41. The process of claim 33 wherein the base is sodium hydroxide, wherein the sodium hydroxide is between about 0.005M and 0.02M and wherein the peroxide oxidizing agent is hydrogen peroxide and is between about 0.005M and 0.02M in the reaction mixture.

42. In a process for the conversion of a D- or L-hexose source to a 3,4-dihydroxybutanoic acid as the salt which comprises:
(a) reacting in a reaction mixture the D- or L-hexose with a first base selected from the group consisting of an alkali metal hydroxide and an alkaline earth metal hydroxide and a peroxide oxidizing agent until 3,4-dihydroxybutyric acid and glycolic acid as the salts from the D- or L-hexose source or 3,4-dihydroxybutyric acid and formic acid as salts are formed as essentially the only products, wherein the peroxide oxidizing agent and the base are present in a range up to a 4 molar excess over the D- or L-hexose and wherein the D- or L-hexose source is between about 0.05 to 80% by weight per volume of the reaction mixture by matched adding of concentrations of the peroxide oxidizing agent and the base simultaneously into the reaction mixture over a period of time which is less than about 5 hours so that at any time during the reaction the concentration of each in the reaction mixture is less than 0.02M with heating at a temperature between about 25° C. and 80° C. to form the salts;
(b) acidifying the reaction mixture to produce an internal cyclic ester; and
(c) heating the internal cyclic ester with a second base selected from the group consisting of an alkali metal hydroxide, an alkaline earth metal hydroxide and mixtures thereof to produce the 3,4-dihydroxybutanoic acid as the salt.

43. The process of claim 42 wherein the internal ester is a lactone.

44. The process of claim 42 wherein in step (b) the ester is removed from the reaction mixture by distillation.

45. The process of claim 42 wherein the 3–4-dihydroxybutanoic acid is (S)-3,4-dihydroxybutanoic acid and the cyclic internal ester is (S)-3,4-dihydroxybutanoic acid gamma-lactone.

46. The process of claim 1 wherein the D- or L-hexose source is a D- or L-glucose source.

47. The process of claim 42 wherein the D- or L-hexose source is selected from the group consisting of maltose, lactose, maltodextrin, starch, starch hydrolysate and cellulose.

48. The process of claim 42 wherein the peroxide oxidizing agent is hydrogen peroxide and the base is sodium hydroxide.

49. The process of claim 48 wherein the sodium hydroxide is between about 0.005M and 0.02M and wherein hydrogen peroxide is between about 0.005M and 0.02M in the reaction mixture.

50. In a process for the conversion of a D- or L-hexose source to a 3,4-dihydroxybutanoic acid as the salt which comprises:
(a) reacting in a reaction mixture the D- or L-glucose with a first base selected from the group consisting of an alkali metal hydroxide and an alkaline earth metal hydroxide and a peroxide oxidizing agent until 3,4-dihydroxybutyric acid and glycolic acid as the salts from the D- or L-glucose or 3,4-dihydroxybutyric acid and formic acid as salts are formed as essentially the only products, wherein the peroxide oxidizing agent and the base are present in a range up to a 4 molar excess over the D- or L-glucose and wherein the D- or L-glucose source is between about 0.05 to 80% by weight per volume of the reaction mixture by matched adding of concentrations of the peroxide oxidizing agent and the base simultaneously into the reaction mixture over a period of time which is less than about 5 hours so that at any time during the reaction the concentration of each in the reaction mixture is less than 0.02M with heating at a temperature between about 25° C. and 80° C. to form the salts;

(b) acidifying the reaction mixture to produce an internal cyclic ester; and (c) heating the internal cyclic ester with a second base selected from the group consisting of an alkali metal hydroxide, an alkaline earth metal hydroxide and mixtures thereof to produce the 3,4-dihydroxybutanoic acid as the salt.

51. The process of claim 50 wherein the reaction in step (a) is continued for at least about 2 hours after the addition.

52. The process of claim 51 wherein the reaction is conducted at about 60° C. for between about 3 and 5 hours.

53. The process of claim 42 wherein the internal cyclic ester is separated from the reaction mixture in step (c).

54. In a process for the preparation of an ammonium salt of 3,4-dihydroxybutyric acid which comprises:

(a) reacting in a reaction mixture the 3,4-dihydroxybutyric acid or salt thereof in an aqueous solution of a base selected from the group consisting of an alkali metal hydroxide, an alkaline earth metal hydroxide and mixtures thereof with a strong acid in an amount between about 0.9 and 3 equivalents based upon the base by addition of the acid to the aqueous solution of the base over a period of time at a temperature of less than about 60° C.; and (b) mixing a polar organic solvent and an amine containing compound selected from the group consisting of an amine, an ammonium salt and mixtures thereof into the reaction mixture in an amount between about 0.9 and 3 equivalents based upon the base to form an ammonium salt of 3,4-dihydroxybutyric acid in the polar organic solvent.

55. The process of claim 54 wherein polar organic solvent containing the ammonium salt of HBA is separated from the reaction mixture and then the ammonium salt of HBA is separated from the polar organic solvent.

* * * * *

UNITED STATES PATENT AND TRADEMARK OFFICE
CERTIFICATE OF CORRECTION

PATENT NO. : 6,239,311 B1
DATED : May 29, 2001
INVENTOR(S) : Rawle l. Hollingsworth Page 1 of 1

It is certified that error appears in the above-identified patent and that said Letters Patent is hereby corrected as shown below:

Column 2,
Line 43, "and" should be -- acid --.
Line 55, "nitrites" should be -- nitriles --.

Column 3,
Line 39, "corresponding y-lactone" should be -- corresponding γ-lactone --.

Column 6,
Line 25, "250°" should be -- 25° --.

Column 9,
Line 65, "mount" should be deleted.

Column 10,
Line 24, "4-dihydroxy-y" should be -- 4-dihydroxy-γ --.
Line 32, " "Stardry 20)" should be -- Stardry 20") --.
Line 41, "4-dihydroxy-y" should be -- 4-dihydroxy-γ --.
Line 44, "y-lactone" should be -- γ-lactone --.

Signed and Sealed this

Fifteenth Day of January, 2002

Attest:

Attesting Officer

JAMES E. ROGAN
*Director of the United States Patent and Trademark Office*